(12) United States Patent
Tyagi et al.

(10) Patent No.: US 7,576,263 B2
(45) Date of Patent: Aug. 18, 2009

(54) GENE OSISAP1 OF RICE CONFERS TOLERANCE TO STRESSES AND A METHOD THEREOF

(75) Inventors: Kumar Akhilesh Tyagi, New Delhi (IN); Mukhopadyay Arnab, New Delhi (IN); Shubha Vij, New Delhi (IN)

(73) Assignee: University of Delhi, New Delhi (IN)

( * ) Notice: Subject to any disclaimer, the term of this patent is extended or adjusted under 35 U.S.C. 154(b) by 0 days.

(21) Appl. No.: 10/540,956

(22) PCT Filed: Dec. 23, 2003

(86) PCT No.: PCT/IN03/00397

§ 371 (c)(1),
(2), (4) Date: Mar. 13, 2006

(87) PCT Pub. No.: WO2004/058963

PCT Pub. Date: Jul. 15, 2004

(65) Prior Publication Data

US 2006/0218677 A1 Sep. 28, 2006

(30) Foreign Application Priority Data

Dec. 31, 2002 (IN) .............................. 1317/DEL/02

(51) Int. Cl.
*C12N 15/82* (2006.01)
*C12N 5/04* (2006.01)
*A01H 5/00* (2006.01)

(52) U.S. Cl. ........................ 800/289; 800/278; 800/295; 800/320.2; 435/468

(58) Field of Classification Search .................. None
See application file for complete search history.

(56) References Cited

FOREIGN PATENT DOCUMENTS

WO    0145492 A    6/2001

OTHER PUBLICATIONS

Mukhopadhyay et al. (NCBI/EMBL, Sequence Accession No. AF140722, Published Jun. 2000).*
Mukhopadhyay et al. (NCBI/EMBL, Sequence Accession No. AF140722, Published Jun. 2000).*
Hiel et al. (The Plant Journal, 6:271-282, 1994).*
Liu et al. (Eur. J. Biochem., 262:247-257, 1999).*
Database EMBL 'Online!, "Oryza sativa (indica cultivar-group) multiple stress-responsive zinc-finger protein mRNA, complete cds.", Jun. 13, 2000, Retrieved from EBI; Database Accession No. AF140722.
Database EMBL 'Online!, "Pathogenesis-related protein.", Oct. 1, 2000, Retrieved from EBI; Database Accession No. Q9LLX1.
Jianyu Song et al., "Isolation and Mapping of a Family of Putative Zinc-finger Protein cDNAs from Rice", DNA Research, vol. 5, pp. 95-101 (1998).
Sangwan et al., "Cold-activation of Brassica napus BN115 promoter is mediated by structural changes in membranes and cytoskeleton, and requries Ca 2+ influx", (2001), vol. 27(1), pp. 1-12, The Plant Journal.
Örvar et al., "Early steps in cold sensing by plant cells: the role of actin cyteoskeleton and membrane fluidity", (2000), vol. 23(6), pp. 785-794, The Plant Journal.
Logemann et al., "Improved method for the isolation of RNA from plant tissues", (1987), vol. 163, pp. 16-20, Analytical Biochemistry.
Lescot et al., "PlantCARE, a database of plant cis-acting regulatory elements and a portal to tools for in silico analysis of promoter sequences", (2002), vol. 30, No. 1, pp. 325-327, Nucleic Acids Research.
Kim et al., "A novel cold-inducible zinc finger protein from soybean, SCOF-1, enhances cold tolerance in transgenic plants", (2001) vol. 25(3), pp. 247-259, The Plant Journal.
Mohanty et al., "Agrobacterium-mediated high prequency transformation of an elite indica rice variety Pusa Basmati 1 and transmission of the transgenes to R2 progeny", (1999), vol. 147, pp. 127-137, Plant Science.
Jani et al., "Expression of Cholera toxin B subunit in transgenic tomato plants", (2002), vol. 11, pp. 447-454, Transgenic Research.

* cited by examiner

*Primary Examiner*—Phuong T Bui
*Assistant Examiner*—Vinod Kumar
(74) *Attorney, Agent, or Firm*—The Webb Law Firm

(57) ABSTRACT

The present invention relates to identification, isolation, characterization and use of a novel gene OSISAP1 obtained from rice and its corresponding novel protein sequence; also relates to a method of over-expressing the novel gene OSISAP1 encoding a zinc-finger stress associated protein from rice conferring salt, cold and drought stress tolerance in transgenic plant systems, further this invention also relates to transgenic plants, plant tissues and plant seeds having a genome containing the novel gene OSISAP1 and a method of producing such plants and plant seeds.

11 Claims, 9 Drawing Sheets

SEQ ID NO. 1

Figure 3:
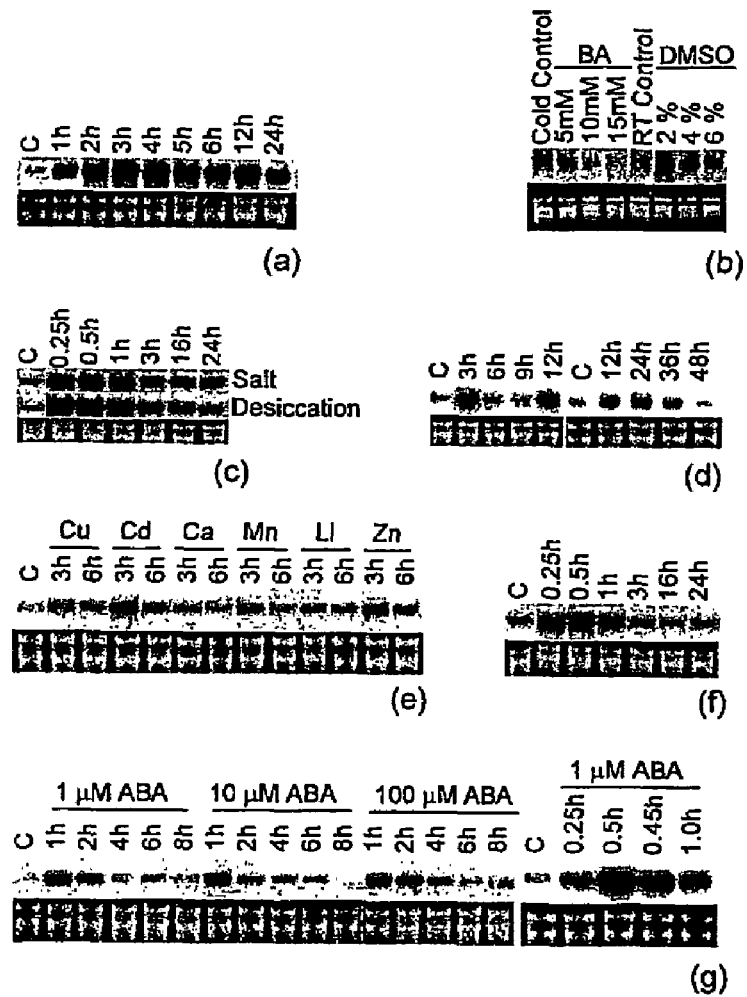

```
gatctctcct gcaatcctca tcacacagca aacccaaacc gcgagcggaa tcctcagcct
gctgagagag cctgagacca agagggggat tctttttttgg ttattgacga tggcgcagcg
cgacaagaag gatcaggagc cgacggagct cagggcgccg gagatcacgc tgtgcgccaa
cagctgcgga ttcccgggca acccggccac gcagaacctc tgccagaact gcttcttggc
ggccacggcg tccacctcgt cgccgtcttc tttgtcgtca ccggtgctcg acaagcagcc
gccgaggccg gcggcgccgc tggttgagcc tcaggctcct ctcccaccgc ctgtggagga
gatggcctcc gcgctcgcga cggcgccggc gccggtcgcc aagacgtcgg cggtgaaccg
gtgctccagg tgccggaagc gtgtcggcct caccgggttc cggtgccggt gcggccacct
gttctgcggc gaacaccggt actccgaccg ccacggctgc agctacgact acaagtcggc
ggcaagggac gccatcgcca gggacaaccc ggtggtgcgc gcggccaaga tcgttaggtt
ctgagaggca aacaaaatta aaaaaaaaat ctactgtttt agcaagaaat ggagaaaaaa
attgggaatt gaaggtgtgg atgttattat tatgctgttc tcttctcgca attgttttttc
ccttttttatt ctttttaatt gcaaacggga ggataagtgg tggaaaagga atagtgtaac
aataatggtg atgtgaggtg gttgagggaa aaagaatcga agaacaaaaa aaaaaaaaaa
aaaa
```

Figure 1

```
  1   gatctctcctgcaatcctcatcacacagcaaacccaaaccgcgagcggaatcctcagcctg
                                                             M  A  Q  R    4
 62   ctgagagagcctgagaccaagagggggattcttttttggttattgacgatggcgcagcgc
       D  K  K  D  Q  E  P  T  E  L  R  A  P  E  I  T  L  C  A  N   24
122   gacaagaaggatcaggagccgacggagctcagggcgccggagatcacgctgtgcgccaac
       S  C  G  F  P  G  N  P  A  T  Q  N  L  C  N  C  F  L  A     44
182   agctgcggattcccgggcaacccggccacgcagaacctctgccagaactgcttcttggcg
       A  T  A  S  T  S  S  P  S  S  L  S  S  P  V  L  D  K  Q  P  64
242   gccacggcgtccacctcgtcgccgtcttctttgtcgtcaccggtgctcgacaagcagccg
       P  R  P  A  A  P  L  V  E  P  Q  A  P  L  P  P  P  V  E  E  84
302   ccgaggccggcggcgccgctggttgagcctcaggctcctctcccaccgcctgtggaggg
       M  A  S  A  L  A  T  A  P  A  P  V  A  K  T  S  A  V  N  R  104
362   atggcctccgcgctcgcgacggcgccggcgccggtcgccaagacgtcggcggtgaaccgg
       C  S  R  C  R  K  R  V  G  L  T  G  F  R  C  R  C  G  H  L  124
422   tgctccaggtgccggaagcgtgtcggcctcaccgggttccggtgccggtgcggccacct
       F  C  G  E  H  R  Y  S  D  R  H  G  C  S  Y  D  Y  S  S  A  144
482   gttctgcggcgaacaccggtactccgaccgccacggctgcagctacgactacaagtcggc
       A  R  D  A  I  A  R  D  N  P  V  V  R  A  A  K  I  V  R  F  164
542   ggcaagggacgccatcgccagggacaacccggtggtgcgcgcggccaagatcgttaggttc
                *
602   tgagaggcaaacaaaattaaaaaaaaaatctactgttttagcaagaaatggagaaaaaaa 662   ttgggaattgaaggtgtggatgttattattatgctgttctcttctcgcaattgttttttcc
722   cttttattcttttaattgcaaacgggaggataagtggtggaaaaggaatagtgtaaca
782   ataatggtgatgtgaggtggttgagggaaaaagaatcgaagaacaaaaaaaaaaaaaaa
842   aaa
```

Figure 2

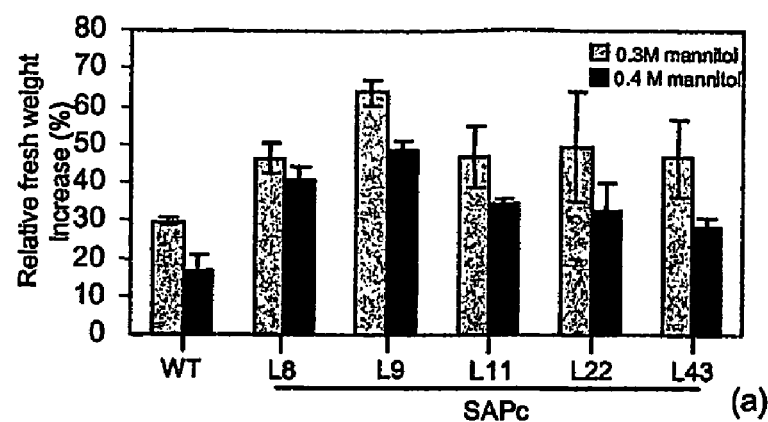
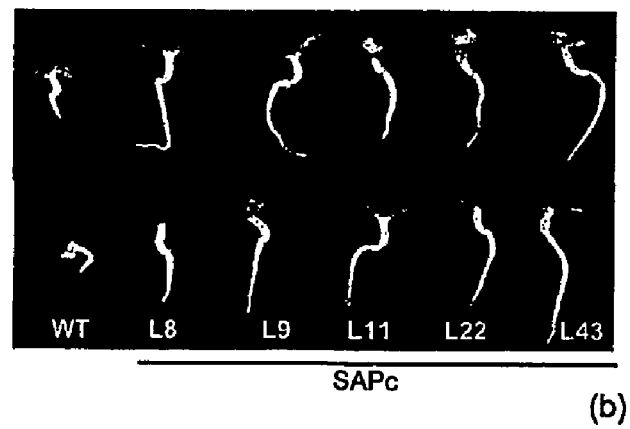
Figure 8

SEQUENCE LISTING

<160> NUMBER OF SEQ ID NOS: 2

<210> SEQ ID NO 1
<211> LENGTH: 844
<212> TYPE: DNA
<213> ORGANISM: Oryza sativa

<400> SEQUENCE: 1

```
gatctctcct gcaatcctca tcacacagca aacccaaacc gcgagcggaa tcctcagcct    60
gctgagagag cctgagacca agaggggat tcttttttgg ttattgacga tggcgcagcg   120
cgacaagaag gatcaggagc cgacggagct cagggcgccg gagatcacgc tgtgcgccaa   180
cagctgcgga ttcccgggca acccggccac gcagaacctc tgccagaact gcttcttggc   240
ggccacggcg tccacctcgt cgccgtcttc tttgtcgtca ccggtgctcg acaagcagcc   300
gccgaggcca gcggcgccgc tggttgagcc tcaggctcct ctcccaccgc ctgtggagga   360
gatggcctcc gcgctcgcga cggcgccggc gccggtcgcc aagacgtcgg cggtgaaccg   420
gtgctccagg tgccggaagc gtgtcggcct caccgggttc cggtgccggt gcggccacct   480
gttctgcggc gaacaccggt actccgaccg ccacggctgc agctacgact acaagtcggc   540
ggcaagggac gccatcgcca gggacaaccc ggtggtgcgc gcggccaaga tcgttaggtt   600
ctgagaggca aacaaaatta aaaaaaaat ctactgtttt agcaagaaat ggagaaaaaa   660
attgggaatt gaaggtgtgg atgttattat tatgctgttc tcttctcgca attgtttttc   720
cctttttatt cttttaatt gcaaacggga ggataagtgg tggaaaagga atagtgtaac   780
aataatggtg atgtgaggtg gttgagggaa aaagaatcga agaacaaaaa aaaaaaaaa   840
aaaa                                                               844
```

<210> SEQ ID NO 2
<211> LENGTH: 164
<212> TYPE: PRT
<213> ORGANISM: Oryza sativa

<400> SEQUENCE: 2

```
Met Ala Gln Arg Asp Lys Lys Asp Gln Glu Pro Thr Glu Leu Arg Ala
1               5                   10                  15

Pro Glu Ile Thr Leu Cys Ala Asn Ser Cys Gly Phe Pro Gly Asn Pro
            20                  25                  30

Ala Thr Gln Asn Leu Cys Gln Asn Cys Phe Leu Ala Ala Thr Ala Ser
        35                  40                  45

Thr Ser Ser Pro Ser Ser Leu Ser Ser Pro Val Leu Asp Lys Gln Pro
    50                  55                  60

Pro Arg Pro Ala Ala Pro Leu Val Glu Pro Gln Ala Pro Leu Pro Pro
65                  70                  75                  80

Pro Val Glu Glu Met Ala Ser Ala Leu Ala Thr Ala Pro Ala Pro Val
                85                  90                  95

Ala Lys Thr Ser Ala Val Asn Arg Cys Ser Arg Cys Arg Lys Arg Val
            100                 105                 110

Gly Leu Thr Gly Phe Arg Cys Arg Cys Gly His Leu Phe Cys Gly Glu
        115                 120                 125
```

```
His Arg Thr Ser Asp Arg His Gly Cys Ser Tyr Asp Tyr Asn Ser Ala
        130                 135                 140
Ala Arg Asp Ala Ile Ala Arg Asp Asn Pro Val Val Arg Ala Ala Lys
145                 150                 155                 160
Ile Val Arg Phe
```

GENE OSISAP1 OF RICE CONFERS TOLERANCE TO STRESSES AND A METHOD THEREOF

FIELD OF THE INVENTION

The present invention relates to identification, isolation, characterization and use of a novel gene OSISAP1 obtained from rice and its corresponding novel protein sequence. This invention also relates to a method of over-expressing the novel gene OSISAP1 encoding a zinc-finger stress associated protein from rice conferring salt, cold and drought stress tolerance in transgenic plant systems. This invention also relates to transgenic plants, plant tissues and plant seeds having a genome containing the novel gene OSISAP1 and a method of producing such plants and plant seeds.

BACKGROUND AND PRIOR ART REFERENCES

Higher plants are sessile organisms. They are rooted to the soil and are unable to move away from harsh environmental conditions. They stand cold winters, hot and dry summers, floods that submerge them, and the salinity of the soil as well as drought that dehydrates them. But, plants have been doing this for millions of years and can adapt to such conditions by making use of an array of mechanisms evolved to fight the stress. They even evolved to either restrict their life-cycle to months that are amenable for growth, or they complete the reproductive phase during those months and enter a phase of restricted metabolism in order to tide over the stressful period. Due to increasing world population and pollution, environmental conditions are changing fast. Increasing need for food and consumer preferences necessitate crop plants to be grown in regions where they are not naturally adapted, leading to various stresses.

Stress in all it forms has negative effects on plant development and productivity. Plants respond to salinity by reduced leaf growth and inhibition of cell division and expansion. The decrease in the osmotic potential of root cells leads to inhibition of water uptake and dehydration of the plants. Subsequently, excessive accumulation of salt leads to death of tissue, organ and eventually whole plant Chilling-stress stunts plant growth, brings about cellular autolysis and senescence, as well as has detrimental effect on flower induction, pollen production and germination. Chilling and desiccation stresses damage cell membranes. Oxidative-stress targets membranes, proteins and DNA.

The development and survival of plants is constantly challenged by changes in environmental conditions, namely fluctuations in temperature, paucity of water, salinity, flooding, metal toxicity and mechanical injury. In order to tide over these adversities, plants elicit complex physiological and molecular responses. Stress is perceived and transduced through a chain of signaling molecules that ultimately affect regulatory elements of stress-inducible genes to initiate the synthesis of different classes of proteins including transcription factors, enzymes, molecular chaperons, ion channels and transporters or alter their activities. Such cascading events controlled by a battery of genes and their intricate regulation help the system to tide over the unfavorable conditions. According to some estimates, plants possess somewhere between 25,000 to 55,000 genes (Kamalay and Goldberg, 1980, 1984; The *Arabidopsis* Genome Initiative, 2001; Burr, 2002; Goff et al., 2002; Yu et al., 2002). Many of these are 'housekeeping' genes that express in all the tissues, while others are organ-specific or regulated by environmental cues. In order to understand the process of development of plants and their response to environmental stresses, it is imperative to know the function of crucial genes and their regulation during different phases of the life cycle (Ausubel, 2002; Ronald & Leung, 2002). Conventional mutation genetics and cloning of the corresponding genes as well as new approaches, like differential screening, subtractive hybridization, differential display, microarray analysis, along with reverse genetics, have been used to clone such genes and define their function (Brent, 2000; Tyagi and Mohanty, 2000; Aharoni and Vorst, 2001).

Rice is the most important food crop as well as a model monocot system (Khush, 1997; Tyagi et al., 1999; Cantrell and Reeves, 2002). However, the production of rice should increase by 60% in next 25 years in order to keep pace with the growing world population. Minimization of the loss due to biotic and abiotic environmental factors can not only help improve net production but extend rice cultivation in marginal and non-cultivable lands (Khush, 1999; Tyagi and Mohanty, 2000). Therefore, the production of a plant, exhibiting tolerance/resistance to various abiotic stress is required. Functional genomics in rice is thus an important area of research whereby function of new genes involved in plant development and survival is defined. Discovery of genes involved in environmental stress responses provides new targets for genetic engineering of rice and other crops for better tolerance/resistance. Therefore, there is a need in isolating and characterizing novel genes of rice and characterizing these novel genes for their various functions. Different screening strategies were employed to isolate genes from elite indica rice (*Oryza sativa* L. var. *Pusa Basmati* 1) that are expressed in an organ-specific manner or are induced by stress. In this invention, we describe the identification, isolation, characterization and use of a novel gene, OSISAP1, encoding a zinc-finger protein that is differentially expressed in various organs and induced by several stresses. This invention also relates to a method of over-expressing the novel gene OSISAP1 encoding a zinc-finger stress associated protein from rice conferring salt, cold and drought stress tolerance in transgenic plant systems. This invention also relates to transgenic plants, plant tissues and plant seeds having a genome containing the novel gene OSISAP1 and a method of producing such plants and plant seeds.

OBJECTS OF THE PRESENT INVENTION

The main object of this invention is to identify, isolate, characterize and use the novel genes that are induced by stress in the various organs of rice.

Another object of the invention is to isolate, characterize and use the OSISAP1 DNA sequence of *Oryza sativa* and identifying as SEQ ID NO: 1

Another object of the invention is to deduce a polypeptide consisting of amino acid sequences as shown in SEQ ID NO: 2, from nucleotide sequence OSISAP1 shown as SEQ ID NO: 1.

Another object of the invention is to construct a plant recombinant vector containing the OSISAP1 DNA sequence from rice under the control of the constitutive CaMV 35S promoter for introducing into various plants.

One more object of the invention is to provide a method of transforming the plant with the said plant recombinant vector DNA to yield transgenic plants which exhibit increased tolerance to various abiotic stresses.

Still another object is to provide a method of modifying tobacco and other plants to increase the tolerance to various abiotic stresses by introducing the novel gene OSISAP1 DNA.

Still another object is to provide a method of modifying tobacco and other plants to increase the tolerance to cold stress.

Still another object is to provide a method of modifying tobacco and other plants to increase the tolerance to drought stress.

Still another object is to provide a method of modifying tobacco and other plants to increase the tolerance to salt stress.

Another object of this invention relates to transgenic plants, plant tissues, plant seeds and their progenies having a genome containing an introduced OSISAP1 DNA sequence of rice as shown in SEQ ID NO: 1.

One more object of the invention is to provide a method of transforming the said DNA fragment with a recombinant vector into plant genome to yield transgenic plants.

Another object of the invention is to provide transgenic plants having increased tolerance to abiotic stress selected from cold stress, drought stress and salt stress.

Yet another object of the invention is to provide a method of producing transgenic plants, plant tissues and plant seeds having a genome containing the novel OSISAP1 DNA.

Yet another object of the invention is to provide a method of producing abiotic stress tolerant plants such as rice, tomato, tobacco etc.

SUMMARY OF THE PRESENT INVENTION

The present invention relates to identification, isolation, characterization and use of a novel gene OSISAP1 obtained from rice which was induced under several stress conditions and its corresponding novel protein sequence.

Another aspect of this invention also relates to a method of over-expressing the novel gene OSISAP1 as shown in SEQ ID NO: 1 encoding a zinc-finger stress associated protein from rice conferring salt, cold and drought stress tolerance in transgenic plant systems. This method involves transformation of plants with the novel gene OSISAP1 under the control of a constitutive promoter. Although any method of transformation can be used, in a preferred embodiment of such a method, an *Agrobacterium tumefaciens* host cell is transformed with a recombinant vector containing the OSISAP1 DNA sequence (SEQ ID NO: 1.) under the control of a constitutive promoter and cultured. The transformed *A. tumefaciens* cell is used to transform a plant cell according to well established procedures known in prior art. As a specific example to illustrate the teachings herein it is disclosed that tobacco, has been successfully transformed with the novel OSISAP1 gene of rice.

The transformed plants exhibit increased tolerance to various abiotic stresses such as cold, drought and salt A further aspect of this invention also relates to transgenic plants, plant tissues and plant seeds having a genome containing the novel gene OSISAP1 and a method of producing such plants and plant seeds.

This invention also relates to a method of transforming plants such as rice, tomato with the novel OSISAP1 DNA for conferring tolerance to abiotic stresses.

DETAILED DESCRIPTION OF THE PRESENT INVENTION

Accordingly, the present invention relates to a novel gene OSISAP1 (SEQ ID NO: 1) obtained from rice and its corresponding novel protein sequence (SEQ ID NO: 2) and also a method of over-expressing the said novel gene OSISAP1 encoding a zinc-finger stress associated protein from rice conferring salt, cold and drought stress tolerance in transgenic plant systems. Further, this invention also relates to transgenic plants, plant tissues and plant seeds having a genome containing the novel gene OSISAP1 and a method of producing such plants and plant seeds.

Stress perception and signal transduction leading to tolerance involve a complex interplay of different gene products. We describe here the identification, isolation, characterization and use of a novel intron-less gene (OSISAP1) from rice encoding a zinc-finger protein that is induced early following different types of stresses, namely cold, desiccation, salt, submergence, heavy metals as well as injury. The gene is also induced by stress hormone abscisic acid. Overexpression of the gene in transgenic tobacco conferred tolerance to salt-, cold- and drought-stress at seedling stage as reflected by the percentage of green seedlings, the fresh weight of seedlings, the developmental pattern and the chlorophyll content. Thus, novel gene OSISAP1 (SEQ ID NO: 1) is an important determinant of stress response in plants.

Abbreviations footnote: OSISAP1, *Oryza sativa* subspecies indica stress-associated protein gene; ABA, abscisic acid; WT, wild type; BA, benzyl alcohol; DMSO, dimethylsulphoxide.

Data Deposition Footnote:

The OSISAP1 cDNA has been deposited in the GenBank database under the accession number AF140722 while the genomic clone has been deposited under accession number AY137590.

The genes and the accession numbers given within brackets of the various sequences which appear in the text are given below:
AWP1 from humans (NM019006);
AWP1 from mouse (AJ251508);
PVPR3 (M75856);
ZNF216 from humans (AF062346);
ZNF216 from mouse (AF062071);

BRIEF DESCRIPTION OF THE ACCOMPANYING DRAWINGS

FIG. 1 Nucleotide sequence of novel gene OSISAP1 (SEQ ID NO: 1) from rice.

FIG. 2 Nucleotide (SEQ ID NO: 1) and deduced amino acid sequence (SEQ ID NO: 2 of OSISAP1 cDNA. Stop codon is marked by an asterisk. Conserved cysteine residues at the N-terminal of the protein involved in forming an A20 type zinc-finger and the C-terminal cysteine and histidine residues of an AN-1 type zinc-finger are shown in bold. The putative N-myristoylation and PKC phosphorylation sites are underlined.

FIG. 3 Expression pattern of OSISAP1 DNA following different stresses to rice seedlings: (a) Cold, (b) Chemical modulators of membrane fluidity, (c) Salt and desiccation, (d) Submergence, (e) Heavy metals, (f) Mechanical wounding, and (g) Abscisic acid (ABA). OSISAP1 cDNA was used as a radiolabeled probe for northern hybridization in all cases. Lower panels in all cases show ethidium bromide-stained rRNA for equivalent loading and RNA quality.

Figure 4:
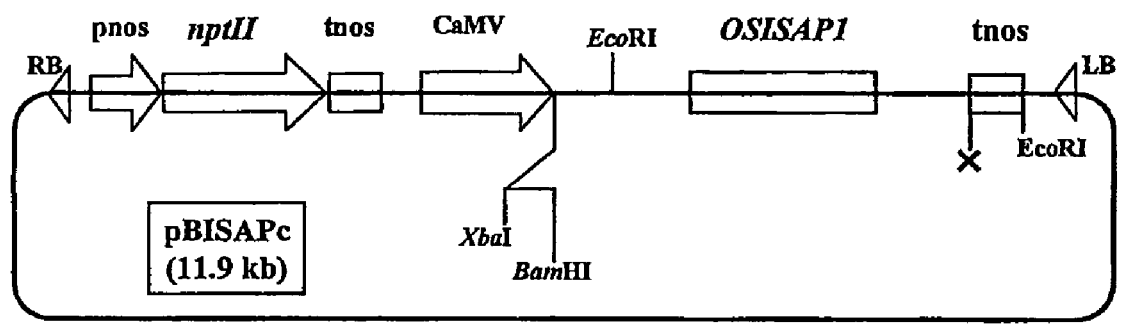

FIG. 4 OSISAP1 DNA cloned in vector pBI121 by replacing 1.87 kb gus fragment to generate construct pBISPAc. The constitutive CaMV35S promoter was used to drive the expression of OSISAP1 DNA. This construct also contained the npt11 fragment which was used for plant selection. This is a schematic representation of the plant recombinant vector, pBISPAc, and is not shown to scale.

Figure 5:
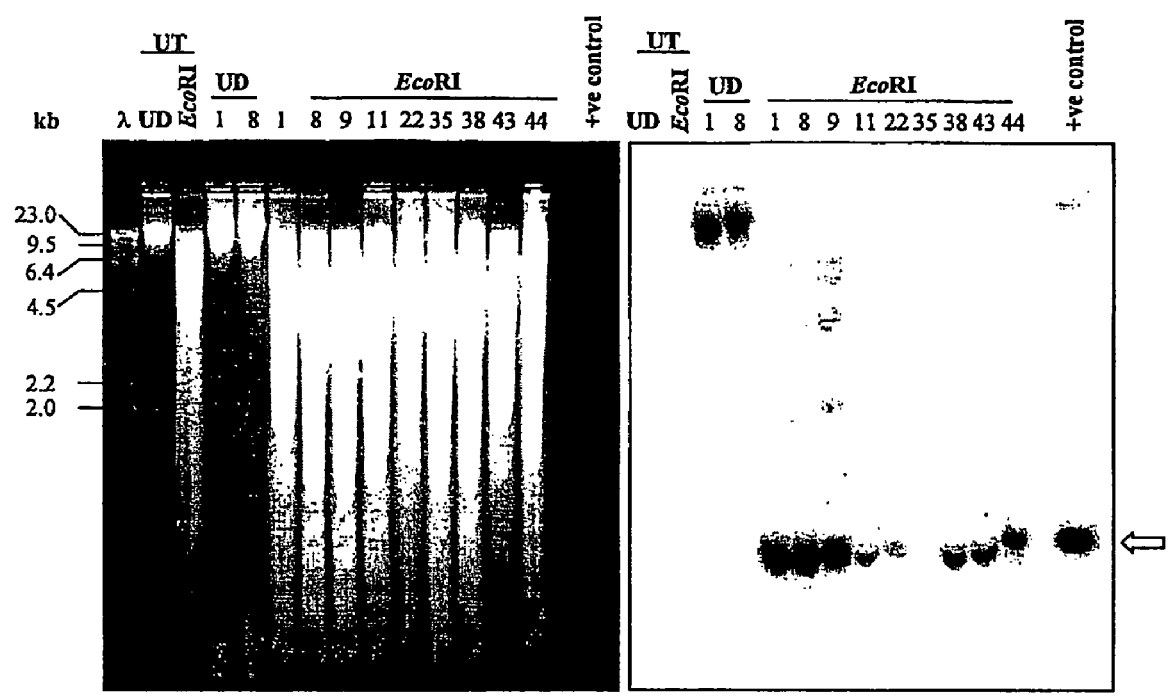

FIG. 5. Southern analysis of putative transformants.

Genomic DNA (10 μg) form wild-type and putative transformants was digested with EcoRI and resolved on 1.2% agarose gel (left panel). Autoradiogram following Southern hybridization with radiolabeled full-length OSISAP1 DNA. The lanes marked as UT and UD stand for untransformed wild-type and undigested DNA, respectively. 25 ng of EcoRI digested pBISAPc was used as positive control. Arrow indicates the expected size (~1 kb) of hybridizing fragment FIG. 6 Determination of expression level of OSISAP1 in different transgenic tobacco lines overexpressing the same under the control of CaMV35S promoter. Northern analysis was performed with 10 μg total RNA from different transgenic lines (SAPcL8, SAPcL9, SAPcL11, SAPcL22 and SAPcL43). UT is untransformed tobacco control. Lower panel shows prominent bands of ribosomal RNA for equivalent loading and RNA quality.

Figure 7:
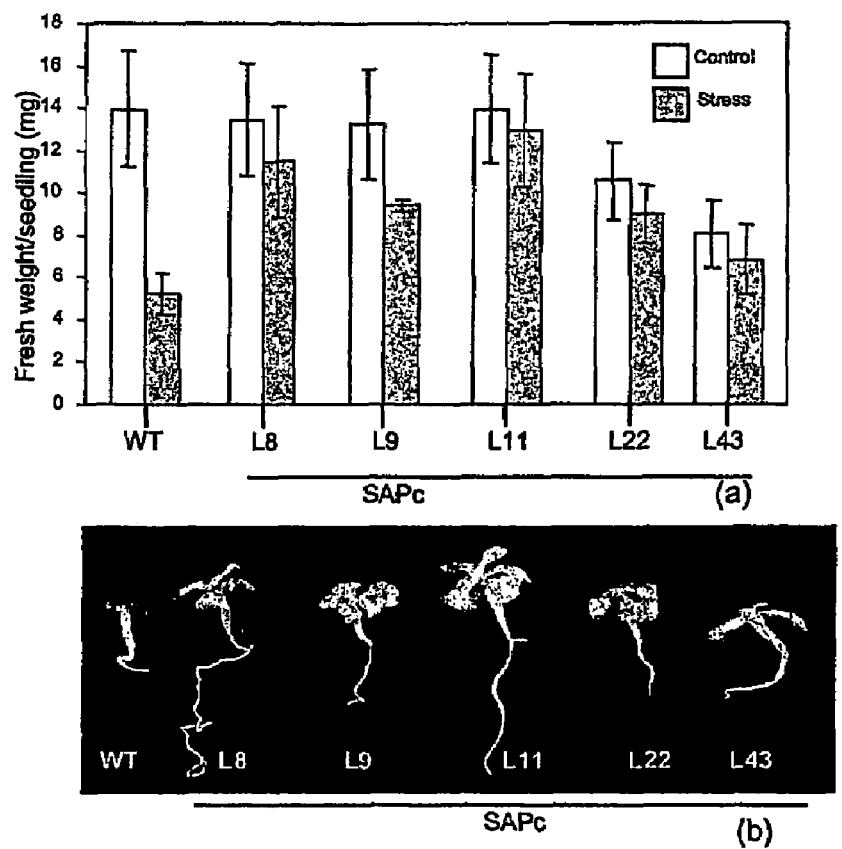

FIG. 7 Effect of cold-stress on tobacco seedlings from wild-type (WT) and OSISAP1 over-expressing transgenic lines (SAPcL8, SAPcL9, SAPcL11, SAPcL22 and SAPcL43). (a) 21-d-old seedlings were grown at 8±1° C. for 15 days and transferred to culture room conditions. Fresh weight was recorded for cold-stressed seedlings after 15 days of cold-stress recovery. Fresh weights of unstressed seedlings of the same age were also recorded and designated as control. Absolute variation of two experiments is shown at the top of each bar. (b) 21-d-old seedlings of untransformed (WT) and OSISAP1 over-expressing lines were cold-stressed at 8±1° C. for 15 days and then transferred back to MSH for recovery. Photographs of representative seedlings of WT and five transgenic lines were taken after 15 days of recovery.

FIG. 8 Effect of dehydration-stress on tobacco seedlings from wild-type (WT) and OSISAP1 over-expressing transgenic lines (SAPcL8, SAPcL9, SAPcL11, SAPcL22 and SAPcL43). (a) Relative fresh weight of 8-d-old seedlings germinated on 0.3 M or 0.4 M mannitol. The fresh weight is shown relative to the fresh weight of unstressed seedlings. Absolute variation of two experiments is shown. (b) Representative seedlings of WT and five transgenic lines taken after 8 days of germination on 0.3 M (upper panel) and 0.4 M (lower panel) mannitol.

Figure 9:
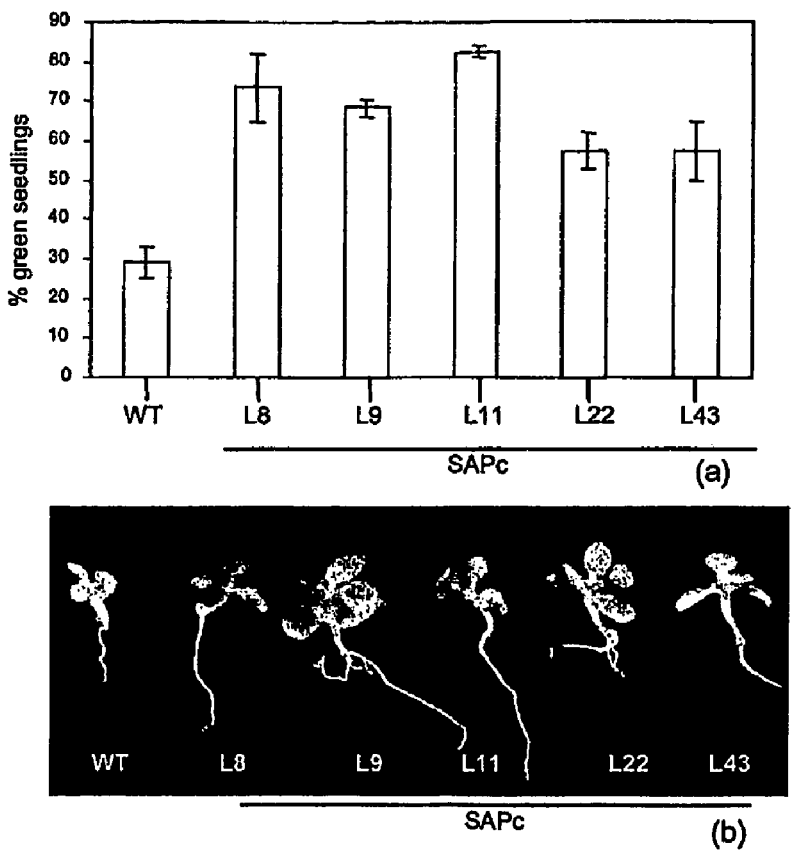

FIG. 9 Effect of salt-stress on tobacco seedlings from wild-type (WT) and T1 progenies of transgenic lines (SAPcL8, SAPcL9, SAPcL11, SAPcL22 and SAPcL43) over-expressing OSISAP1. (a) 21-d-old seedlings were salt-stressed in 250 mM NaCl for 4 days and then transferred back to MSH for recovery. After 8 days of recovery, seedlings of WT and transgenic lines that retained green colour were counted. Absolute variation in two experiments is shown at the top of each bar. (b) 21-d-old seedlings were stressed with 250 mM NaCl for 4 days and then transferred back to MSH for recovery. Photographs of representative seedlings of WT and five transgenic lines were taken after 8 days of recovery.

BRIEF DESCRIPTION OF THE SEQUENCES IN THE SEQUENCE LISTING

SEQ ID NO: 1 Nucleotide sequence of novel gene OSISAP1 from rice encoding zinc-finger stress associated protein.

SEQ ID NO: 2 Deduced amino acid sequence of OSISAP1.

The present invention was initiated with a view to identify novel genes and regulatory elements from rice. Out of several genes initially isolated, one gene has been major target of this investigation. The novel gene OSISAP1 (SEQ ID NO: 1) isolated from rice is induced by various stresses and codes for a novel stress-associated protein.

In an embodiment of the invention provides a method to identify and isolate genes that are differentially expressed in a particular organ of rice or during a certain developmental stage. In this direction, a multi-pronged strategy was employed. Apart from reverse northern and differential screening, northern screening of randomly selected cDNA clones was performed in order to isolate differentially expressing genes. Three cDNA libraries from different tissues, namely pre-pollination or post-fertilization stage inflorescence and roots of 7-d-old seedlings of rice, were constructed in the laboratory in Lambda ZAP vector (Stratagene, USA). The root cDNA library was plated at low density on NZY medium and individual plaques were lifted. Following single clone excision, the recombinant phage clones were converted into phagemids having the cloned cDNA inserts. These inserts were checked by restriction digestion with EcoRI and XhoI, which released the insert form the vector backbone. The cDNA clone inserts were then used as radiolabeled probes to hybridize to the northern blots prepared from total RNA isolated from roots or shoots of 7-d-old seedlings and pre-pollinated spikelets. Clones that were showing organ-specific or differential expression were sequenced with standard primers. The partial cDNA sequences were used to search the GenBank database for homology with known entries. Using this strategy, three differentially expressing clones were identified from the root cDNA library, one of them was OSISAP1, coding for a novel stress-associated protein. OSISAP1 mRNA was detected at much higher level in the root and pre-pollination stage spikelets as compared to shoot. This clone was characterized in detail at the molecular level, in the present invention.

Analysis of the cDNA Sequence and the Deduced Polypeptide

The cDNA was initially sequenced from both ends using standard vector-specific primers. For sequencing both strands, the cDNA was subcloned using internal restriction enzyme sites. The sequences were aligned using Clustal method (for multiple sequence alignment) finally, an assembled cDNA sequence of 844 bp named OSISAP1 (SEQ ID NO: 1) emerged (FIG. 1) and was submitted to GenBank under the Accession no. AF140722. The cDNA was translated in silico, in all the three reading frames, using standard methods. The +1 open reading frame was selected as it gave a long and continuous amino acid sequence starting with methionine. The cDNA had a 19 bp poly-A tail. The cDNA is 57.2% GC rich, when the poly-A is not considered. The open reading frame is terminated by a UGA stop codon. The open reading frame codes for a protein of 164 amino acids (SEQ ID NO: 2, FIG. 2) with a predicted molecular weight of 17.6. kDa. It showed homology to several zinc-finger proteins, including the human and mouse PRK1-associated protein AWP1 (Duan et al., 2000), PVPR3 (Sharma et al., 1992), human and mouse zinc-finger proteins ZNF216 (Scott et al., 1998), *Xenopus* ubiquitin-like fusion proteins, XLULFP and AFULFP (Linnen et al., 1993) and the ascidian posterior end mark (PEM6) protein (Satou and Satoh, 1997). All these proteins showed homology to OSISAP1 (SEQ ID NO: 2) in the zf-AN1 region, which is present at the carboxy-terminus of the protein, stretching between amino acids 100 and 164 (FIG. 2).

It has a consensus sequence of $Cx_{2-4}Cx_{9-12}Cx_2Cx_4Cx_2Hx_5HxC$ (SEQ ID NO: 3), where x represents any amino acid. However, several other amino acids were found to be invariant in this domain. The conserved cysteine and histidine residues may form a single zinc-finger. Towards the amino-terminus, there are four cysteine residues (at amino acids 22, 26, 38 and 41, FIG. 2) that are conserved between OSISAP1 (SEQ ID NO: 2), AWPL (Acc no.NM019006, AJ25 1508) and ZNF216 (Acc no.AF062346, AF062071). This region is similar to the A20 (an inhibitor of cell death)-like zinc-fingers, which mediate self-association in A20 (De Valck et al., 1996). OSISAP1 also has about 51% identity over a stretch of 40 amino acids (56-96) to the human transcription factor NFκB p65 subunit consensus sequence (Ruben et al., 1991). The homology is towards the C-Terminus of the human protein, between amino acids 370 and 410.

Predicted proteins similar to OSISAP1 are found in other plant species like *Arabidopsis* and *Prunus*, but the similarity is mainly due to the conserved zinc-fingers. OSISAP1(SEQ ID NO: 2) sequence showed maximum homology (79% identity) to PVPR3 (Acc. no. M75856) (*Phaseolus vulgaris* pathogenesis-related protein) zinc-finger. The protein has no signal sequence and is possibly a soluble intra-cellular protein. The protein is rich in alanine (14.02%) and proline (10.98%). There are 17 acidic amino acids and 34 basic amino acids, making it a basic protein of estimated pI 8.64. The amino acid sequence has a potential protein kinase C phosphorylation site at amino acid position 30 and a N-myristoylation site at amino acid position 132 (FIG. 2). OSISAP1 (SEQ ID NO: 1) is a single copy gene as determined by Southern analysis.

Rice Genomic DNA Library

In order to isolate genomic clones to unravel genomic level organization and characterize the regulatory region of OSISAP1, a rice genomic DNA library was prepared. High molecular weight (~100 kb) genomic DNA isolated from dark-grown rice (variety Pusa Basmati 1) was used for preparing genomic DNA library using Lambda DASH II vector (Stratagene, USA). Pilot restriction digestions set up with 1 μg genomic DNA and varying concentrations of a four base cutter restriction enzyme, MboI, for 30 min gave the desired amount of digestion. The concentration of enzyme (0.75 μl of 0.25 U/μl MboI) that gave maximum smear of genomic DNA in the range of 23 to 9 kb, with about 30% of the DNA in the undigested form, was chosen. Large-scale restriction digestion was set up by scaling up the reaction. About 100 μg DNA was digested for 25 min and the DNA was then purified by phenol-chloroform extraction. An aliquot of the digested DNA was resolved on agarose gel along with undigested DNA. In order to obtain the fraction (9-23 kb) most suitable for ligation to the Lambda DASH II vector, sucrose gradient ultracentrifugation was performed using the digested DNA. The CIAP-treated and purified DNA, following size fractionation, was resolved on a 0.8% agarose gel and the DNA in the size range of 9-23 kb was selected and purified for ligation. Following ligation to vector and packaging into phage particle, the primary library was titered. The primary library was found to be having >5×10$^5$ pfu. The average insert size of the library was then determined by digesting several randomly selected phage clones with EcoRI. The average insert size was calculated to be ~17 kb.

Isolation of OSISAP1 Genomic Clone

To isolate the genomic clone of OSISAP1, the genomic library prepared in Lambda DASH II was screened with the full-length cDNA of OSISAP1 as the radiolabeled probe. Primary round of screening produced two positive clones. They were purified by two more rounds of screening. All the plaques plated in the tertiary round gave signals, indicating that they are positive and homogeneous.

Subcloning and Sequencing of the Genomic Clone

The ~6.0 kb EcoRI fragment (designated SAPg3E6), giving positive signal upon Southern hybridization, was cloned in pBlueScript SK$^+$ (Stratagene, USA) and the recombinant clone was named as pBSSAPg3E6. Southern hybridization was performed using the full-length OSISAP1 cDNA as the probe to identify the DNA fragment within the recombinant lambda clone this indicated a 2.9 kb Pst1 fragment which showed hybridization to the cDNA clone. The 2.9 kb fragment was sub-cloned and sequenced using standard procedures. The sequence analysis indicated that the reading frame was uninterrupted, i.e. without any intron. These sequences were aligned using the CLUSTAL method for multiple sequence alignment and submitted to GenBank under the accession no. AY137590.

OSISAP1 is single copy gene as determined by Southern analysis. However, when the *indica* rice database hosted at the University of Beijing, Center for Genomics and Bioinformatics, was searched with the OSISAP1 coding region, two contigs were found to have sequences with significant homology to OSISAP1. Contig 46636 showed 97% homology at the nucleotide level and represents essentially the same gene. Contig 10325, on the other hand, showed 59% homology at the nucleotide level and 64% homology at the level of deduced amino acid. It remains to be seen whether Pusa Basmati 1 also has a similar gene that was not detected under the stringency conditions used for Southern hybridization. The coding region of the genomic clone of OSISAP1 is continuous, without an intron. The start site of transcription was mapped to a G nucleotide, 126 bp upstream of ATG. When the genomic region upstream of the transcription start site was analyzed in silico, several cis-acting elements involved in stress-responsive gene expression, like CRT/DRE, ABRE, HSE, wound-responsive element, GT box, ethylene-responsive element and GC motifs were identified (Thomashow et al., 1999; Zhu et al., 2002; Lescot et al., 2002).

OSISAP1 is developmentally regulated. OSISAP1 gene was in fact identified during a screen for differentially expressing organ-specific genes. It was found to express at an elevated level in the stem of mature plants, rachis and pre-pollinated spikelets. The level of expression was low in the post-fertilized spikelets. The roots of young plants had higher transcript abundance than that of the mature plants. However, the level of transcript of this gene was higher in leaves of mature plants.

Stress-induced expression of OSISAP1. OSISAP1 is induced under several abiotic stresses. The transcript levels increased to a very high level within 1 h following cold treatment to the seedlings (FIG. 3a). The level continued to increase till 3 h, remained practically unaffected till 12 h and decreased thereafter. The cold-induced membrane rigidification is considered to be the primary event in cold perception by plants (Örvar et al., 2000; Sangwan et al., 2001). The event of membrane rigidification at low temperature can be prevented by benzyl alcohol (BA) that acts as a membrane fluidizer or may be simulated at room temperature by treatment with a membrane rigidifier, dimethylsulphoxide (DMSO). With a view to study the role of membrane rigidification on OSISAP1 expression, effect of BA and DMSO were examined. Leaves of nine-day-old seedlings were treated with different concentrations of BA and exposed to cold temperature. The cold-induced accumulation of OSISAP1 was dramatically reduced by the inhibitor of membrane rigidification (FIG. 3b). On the other hand, treatment of seedlings with membrane rigidifier DMSO significantly increased OSISAP1 expression at room temperature (FIG. 3b). However, with higher concentrations of DMSO, induction was relatively less, possibly due to the toxic nature of the chemical. In case of salt-stress, transcript levels peaked as early as 15 min and declined after 1 h (FIG. 3c). However, even at 24 h, mRNA level was more than that of the control. Similar pattern of transcript accumulation was observed for desiccation stress (FIG. 3c). In case of submergence-stress, different induction kinetics was observed (FIG. 3d). The gene was induced strongly within 3 h following which its mRNA level declined dramatically to the level of the control. But, the mRNA level peaked again at 12 h and stayed high till 36 h, showing a decline thereafter. The gene was also found to be responsive to different heavy metals (FIG. 3e). Essentially, treatment with copper, cadmium, manganese or zinc salts led to significant increase in transcript abundance by 3 h and at 6 h a decline was evident. Calcium and lithium salts had only marginal effect on the mRNA level. The gene was also responsive to mechanical injury (FIG. 3f). The gene responded to ABA at concentrations as low as 1 µM (FIG. 3g); the expression of OSISAP1 peaked at 30 min following treatment of seedlings with 1 µM ABA. But, with increasing concentration of ABA, the steady-state transcript level was maintained for longer duration.

Germplasm-specific Expression

In order to investigate the response of OSISAP1 to different abiotic stresses in germplasm-specific manner, different abiotic stress-tolerant or -sensitive lines were obtained. Drought-tolerant cultivar Tulasi, drought-sensitive Triguna, salt-sensitive Jaya and salt-tolerant Vikas were used in this study. Pusa Basmati 1 was kept as a sensitive control. They were subjected to either salt- or desiccation-stress at seedling stage. No significant correlation could be drawn between the tolerance of the cultivar/variety to the level of induction of OSISAP1 transcript following either of the two stresses evaluated. However, it was found that all the germplasm of rice evaluated possesses OSISAP1 and the gene was induced following drought- and salt-stresses in all these cases.

Cloning of OSISAP1 in pBI121 and Transformation of Tobacco

Since OSISAP1 is induced by several stresses it was used for transforming a model plant tobacco for functional analysis of this novel gene. In order to over-express rice novel gene OSISAP1 gene in tobacco, the cDNA was cloned in pBI121 (Clontech, USA). The vector has CaMV35S promoter driving the expression of gus gene. For cloning the OSISAP1 cDNA, the gus gene was replaced. Initially, the vector was digested with SacI, which cuts at the 3' of gus. The ends of the DNA were polished with T4 DNA polymerase, in the presence of all the four dNTPs. The vector was then cut with BamHI. This released the gus gene from the vector backbone. The vector was purified by gel extraction. On the other hand, the pBK-CMV harbouring the OSISAP1 cDNA was cut first with XbaI, the DNA end-filled with T4 DNA polymerase and all four dNTPs, and then digested with BamHI. This released the cDNA with 3' blunt-end and 5' end having BamHI. The fragment was ligated to the pBI121, having compatible ends. The resulting vector, pBISAPc, has CaMV35S promoter driving OSISAP1 cDNA. The selectable marker, nptII, is driven by the nos promoter. Restriction digestion with EcoRI releases cDNA along with the nos terminator, while BamHI linearizes the recombinant clone showing that the site is restored following cloning. A diagrammatic representation of the entire construct in plant transformation vector is shown in FIG. 4.

This construct was then mobilized into Agrobacterium by chemical transformation. The presence of the construct was detected by plasmid isolation and restriction digestion. The construct in Agrobacterium was mobilized in tobacco (Nicotiana tabacum var Xanthi). The regenerating shoots, in the presence of 200 mg/l kanamycin, were transferred to rooting medium containing same concentration of kanamycin. Following root development, plants were transferred to pots and maintained in culture room.

Confirmation of Transgenics and Expression of the Transgene

Firstly, nptII assay was performed on the putative transformants to detect the activity of neomycin phosphotransferase II, the selectable marker used, in the total protein. A confirmed transgenic and an untransformed tobacco were used as positive and negative controls, respectively. Eight transgenic lines (SAPcL1, SAPcL8, SAPcL9, SAPcL38, SAPcL22, SAPcL11, SAPcL44 and SAPcL43) showed the activity of the nptII.

These lines were also checked for the presence of transgene by Southern analysis (FIG. 5). Genomic DNA isolated from the putative transformants was digested with EcoRI. The enzyme has sites at the 5' end of the cDNA and at the 3' end of the nos terminator, in pBISAPc. A fragment of ~1 kb corresponding to the OSISAP1 cDNA along with nos terminator is released on digesting with EcoRI. Band corresponding to the expected size of ~1 kb was detected in the positive control plasmid, as well as in the transgenic lines (indicated by an arrow in FIG. 5), but not in the untransformed control and SAPcL35, which showed no nptII activity.

Figure 6:
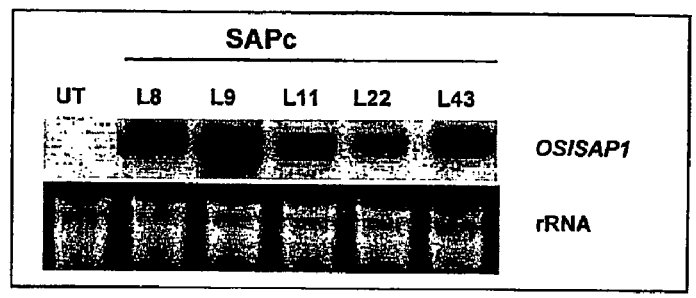

Northern analysis was performed with selected five lines to determine the level of transgene expression FIG. 6). RNA was isolated from leaves and hybridized to full-length OSISSAPI as the radiolabeled probe. It was also noted that the RNA from wild-type tobacco did not hybridize to OSISAP1 probe.

Cold, salt and drought stress tolerance of transgenic tobacco seedlings harboring OSISAP1. Five independent transgenic lines (SAPcL8, SAPcL11, SAPcL22, SAPcL9 and SAPcL43) of tobacco harboring the pBISAPc and constitutively expressing OSISAP1 were analyzed for salt tolerance in the T1 generation. For analysis of stress tolerance, the transgenic lines were grown without selection agent in medium. The contribution of kanamycin sensitive (segregating, non-transgenic) seedlings that did not harbor the transgene was excluded from the total number of seedlings analyzed for each line to assess stress tolerance.

Five transgenic lines (SAPcL8, SAPcL11, SAPcL22, SAPcL9 and SAPcL43) harboring the OSISAP1 gene were also analyzed for cold tolerance in the T1 generation. Phenotypically, transgenic seedlings were more healthy after stress (FIG. 7 a, b). In case of transgenic seedlings, the third or fourth leaf had already emerged, while in WT, only the first two leaves could be observed (FIG. 7b). The measurement of fresh weight of seedlings after 15 d recovery revealed that stressed transgenic seedlings gain 67% to 92% fresh weight while WT gains only 35% fresh weight compared to unstressed seedlings (FIG. 7a.). Further, the fresh weight of transgenic seedlings was always better than WT seedlings at low temperature. Evaluation of OSISAP1 over-expressing lines for drought-stress tolerance revealed that the percentage germination of WT was much lesser compared to transgenics over an 8-day period. On day 8 of exposure to 0.3 M mannitol, only 60% of WT germinated while 90% or more germination was seen in all transgenic lines except line 22 which showed 69% germination. When germinated on 0.4 M mannitol, only 41% germination was seen in WT while transgenics showed between 69-92% germination. Also, the fresh weight of stressed transgenics was much better compared to that of WT as reflected on quantitative estimation and qualitatively (FIG. 8a, b).

For determining the effect of OSISAP1 overexpression on the salt tolerance of transgenic tobacco, transgenic and untransformed (WT) seedlings were grown as described in Materials and Methods. No significant difference was observed in fresh weight of wild type (WT) and transgenic seedlings on the day of exposure to stress (Tables 1). After 4 d of transfer, although chlorosis started both in WT and transgenic lines, it was much less in transgenic plants as they retained more chlorophyll and thus green colour (FIG. 9) following stress. Highly significant improvement in fresh weight gain of seedlings from transgenic lines under stress was observed. After 8 d of recovery, fresh weight of stressed WT plants recovered to the level of unstressed plants, although their chlorophyll content remained lower. The appearance of transgenic seedlings was much better than the WT after 8 d of stress-recovery and they resumed vegetative growth faster (FIG. 9a, b).

The analysis of the transformed plants to various stresses clearly show that transformed plants have better growth and percentage survival as compared to the untransformed controls under various stressful conditions such as cold, drought and salt stresses.

There are a number of examples wherein studies on plant molecular biology and genetic engineering for changing the metabolic pathway and stress has been tested in model plant such as tobacco or *Arabidopsis* and then shown to yield similar phenotypes in other important crop plants. We have transformed rice and tomato with the novel gene OSISAP1 for conferring increased tolerance to cold, drought and salt stress (Mohanty et al., 1999 and Jani et al., 2002) These results show that the novel gene OSISAP1 (SEQ ID NO: 1) confers increased tolerance to stresses and growth advantages to the transformed plants as compared to the untransformed control.

A large number of genes are induced following exposure to various abiotic stresses (Seki et al., 2001). These genes function in various ways to confer stress tolerance to plants (Ingram and Bartels, 1996; Thomashow, 1999; Hasegawa et al., 2000b; Zhu, 2002). The expression patterns of these genes are governed by the need of the system, i.e. genes that are required during early phases of stress response are induced soon after stress while those required during homeostasis and recovery are induced later. Kawasaki et al. (2001) compared the gene expression profiles following salt-stress in contrasting rice varieties Pokkali (salt-tolerant) and IR24 (salt-sensitive). The response to salt was categorized as instantaneous (within 15 min), early (1 h), early recovery (3-6 h) and stress compensation (after 24 h) with 8-10 upregulated or downregulated genes in each category. In this context, OSISAP1 gene (SEQ ID NO: 1) falls in the instantaneous response category, as the gene is induced to high levels within 15 min of exposure to stress. Its protein product (SEQ ID NO: 2) may be required very early following stress. Such early induction of gene expression has also been observed for desiccation and salt induction of RD29 (Yamaguchi-Shinozaki and Shinozaki, 1993, 1994), desiccation induction of COR47 and ERD10 (Welin et al., 1994; Kiyosue et al., 1994), salt induction in case of OSLEA3 (Moons et al., 1997) as well as desiccation, salt or ABA induction of RD22 (Abe et al., 1997). The OSISAP1 protein (SEQ ID NO: 2) has homology to a mammalian protein A20 (Opipari et al., 1990). The zinc-finger domain of A20 is required for dimerization (De Valck et al., 1996) and it inhibits the TNF-induced apoptosis through inhibition of NF-κB mediated gene expression (Cooper et al., 1996; Heyninck et al., 1999a, b; Beyaert et al., 2000; Lademann et al., 2001). It was shown that the zinc-finger domain of A20 protein is sufficient for its inhibitory activity, independent of binding to other cellular proteins (De Valck et al., 1997; Lademann et al., 2001). It has also been shown that overexpression of A20 or even the A20 C-terminal zinc-finger domain in cultured cells down-regulated NF-κB activity (Song et al., 1996; Evans et al., 2001). High salinity stress leads to inhibition of cell division and acceleration of cell death (Hasegawa et al., 2000) while chilling stress leads to wilting and chlorosis of tissues and electrolyte leakage (Tokuhisa and Browse, 1999). All these would ultimately lead to cell death. Overexpression of OSISAP1gene can help avoid chlorosis and cell death in transgenic plants. The stressed plants have lower levels of stress-associated injuries and can recover faster. Thus, although in two different systems, and with only a zinc-finger motif common between the two, OSISAP1 and A20 have similar effects when overexpressed. The protein OSISAP1 also shows high homology of its second C-terminal zinc finger domain with AN-1 type of zinc finger proteins. These proteins, PEM6, ZNF216, XLULFP and PVPR3, have no defined function. Several hydrophilic polypeptides are induced during cold acclimation and remain soluble upon boiling (Hughes and Dunn, 1996; Thomashow, 1998). They are speculated to contribute to freezing tolerance by mitigating the harmful effects of dehydration associated with freezing. Salt stress as well as cold stress also leads to dehydration at cellular levels (Hasegawa et al., 2000). OSISAP1 protein is hydrophilic and this property may also contribute to the increased salt and cold tolerance in transgenic plants. As shown by the present investigation, overexpression of several other genes has earlier been found to provide stress tolerance to seedlings (Prändl et al., 1998; Saijo et al., 2000; Kim C K et al., 2001; Piao et al., 2001; Sun et al., 2001; Tamminen et al., 2001).

In conclusion, this invention has identified and characterized a novel zinc-finger protein gene from rice and unraveled a novel determinant of salt, drought and cold tolerance that may be used to engineer stress tolerance in other crop plants. It has also not escaped our notice that the protein may have function in other stresses, which have been shown to induce its expression.

The following examples are for illustration purpose only and should not be construed to limit the scope of the invention.

EXPERIMENTAL PROCEDURES

Plant Materials and Treatments

Rice (*Oryza sativa* subsp. *indica* var. Pusa Basmati 1) seeds were treated and grown as described previously (Grover et al., 1999). After 7 days of growth, the seedlings were transferred to 100 ml beakers containing cotton soaked in water, while for other treatments water containing the desired solute was used. Sodium chloride was added at a final concentration of 200 μM. ABA (Sigma) was dissolved in DMSO to make a stock of 10 mM and was further diluted in water. Injury to the seedlings was inflicted by clipping the leaf margins at ~1 cm intervals. For cold shock, the seedlings were maintained at 5±1° C. Desiccation was simulated by drying the plants on tissue paper and keeping them wrapped in dry tissue paper for desired time. Seedlings growing in a 100 ml beaker were kept submerged under water in a 2 L glass beaker. Cut leaves of nine-day-old seedlings were treated with 5, 10 and 15 mM benzyl alcohol (BA) at 25° C. for 3 h and then the treatment was continued at 5±1° C. for 48 h (Sangwan et al., 2001). For treatment with DMSO, cut leaves of seedlings were kept at 25° C. for 6 h in the presence of 2, 4 and 6% DMSO.

Cloning and Sequence Analysis of OSISAP1 Gene

A cDNA library from roots of 7-d-old rice seedlings was prepared in Lambda ZAP Express vector (Stratagene, USA). Random clones were picked from the library and single clone excision was performed to obtain recombinant pBK-CMV phagemid vector, as per manufacturer's instruction. These clones were used as radio-labeled probes and hybridized to total RNA isolated from different parts of rice plant. Several clones that were expressing differentially in various organs were identified and further characterized.

One of them, OSISAP1, was sequenced from both ends with standard primers. In order to obtain the full sequence, the cDNA was digested either with Sac1 and religated or Pst1 and subcloned in pBlueScript SK+. Subclones were sequenced using standard primers using standard methods.

In order to isolate the genomic clone of OSISAP1, a rice genomic DNA library was prepared in λDASH II vector (Stratagene, USA) using Mbo1digested genomic DNA. The cDNA was used to generate radiolabeled probe and screen the library (Sambrook et al., 1989). Positive plaques were purified by three rounds of screening and a 5.5 kb sub-cloned fragment, from a recombinant phage clone, containing the gene was sequenced. Transcription start site was determined by primer extension analysis using primer designed encompassing the translation start site (Sambrook et al., 1989).

Isolation of plasmid DNA, restriction digestions, ligations of DNA, PCR, agarose and acrylamide gel electrophoresis, transformation and culture of *E. coli*, sequencing of various DNA fragments were carried out according to standard procedures as described by Sambrook et al., 1989. The cDNA of OSISAP1 (SEQ ID NO: 1) is of 844 bp including a 19 bp poly-A tail and codes for a protein of 164 amino acids with a predicted molecular mass of 17.6 kDa (SEQ ID NO: 2).

RNA Blot Analysis.

RNA extraction was performed according to Logemann et al. (1987) with minor modifications. Northern analysis was carried out with 20 µg of total RNA according to Grover et al. (1999). The $\alpha^{32}$-P dATP labeled OSISAP1 cDNA was used as a probe. Hybridization was detected by autoradiography. Ethidium bromide-stained rRNA bands from identical samples served as control for total RNA quantity and quality.

Construction of Plant Transformation Vector for Constitutive Expression in Plants In order to overexpress rice OSISAP1 (SEQ ID NO: 1) in tobacco (*Nicotiana tabacum* var Xanthi), the cDNA was cloned in pBI121 (Clontech, USA), by replacing the gus gene. Initially, the vector was digested with SacI, which cuts at the 3' of gus. The ends of the DNA were polished with T4 DNA polymerase, in the presence of all the four dNTPs. The vector was then cut with BamHI to release the gus gene from the vector backbone. The vector was purified by gel extraction. On the other hand, the pBK-CMV harbouring the OSISAP1 (SEQ ID NO: 1) cDNA was cut first with XbaI, the DNA end-filled with T4 DNA polymerase and all four dNTPs, and then digested with, BamHI. This released the cDNA with 3' blunt-end and 5' end having BamHI. The fragment was ligated to the pBI121 having compatible ends. The resulting vector, pBISAPc, has CaMV35S promoter driving the expression of OSISAP1 gene (SEQ ID NO: 1) is shown in FIG. 4. The plant selectable marker was gene for kanamycin resistance. This construct was then mobilized into *Agrobacterium tumefaciens* strain LBA4404 by chemical transformation.

Plant Transformation

*Agrobacterium*-mediated transformation of tobacco (*Nicotiana tabacum* var Xanthi) was carried out as per standard protocol (Gelvin et al., 1994). The regenerated shoots, in the presence of 200 mg/l kanamycin, were transferred to rooting medium containing the same concentration of kanamycin. Following root development, plants were transferred to pots and maintained in culture room. Firstly, nptII assay was performed on the putative transformants to detect the activity of neomycin phosphotransferase II, the selectable marker used, in the total protein. The integration and expression of transgene in different lines was confirmed by Southern (FIG. 5) and northern analysis (FIG. 6), respectively, using OSISAP1 cDNA as a radiolabeled probe. The Southern and northern analysis was carried out using standard procedures as described by Sambrook et al., 1989. The transgenic lines over-expressing OSISAP1 have been propagated to the T2 generation.

Similarly, rice transformation using the novel gene OSISAP1 was carried out using the standard protocol. Tomato plants over-expressing this gene were obtained using the standard protocol.

Analysis of Transgenics for Salt-, Cold- and Drought-stress Tolerance.

Wild type and T1 seeds of transgenic tobacco were surface-sterilized with 70% ethanol in a microcentrifuge tube for 30 s with constant agitation, under a laminar flow hood. Following the treatment, ethanol was removed using a pipette. The seeds were immersed in 2% (v/v) sodium hypochlorite solution containing a drop of Tween 20, for 5 min, agitated occasionally by tapping the microcentrifuge tube and subsequently washed at least six times with autoclaved Milli-Q water. The seedlings were grown in medium containing half strength MS medium without sucrose and organic ingredients (MSH) for 16 d in a culture room maintained at 25±1° C. under 16 h/8 h light/dark cycle and each rack was illuminated with light (50-100 µmol m$^{-2}$ s$^{-1}$) provided by three white fluorescent tubes (Philips Champion 40 W/54) and one yellow fluorescent tube (Philips Trulight 36 W/82). The 16-d-old seedlings were transferred to fresh MSH and allowed to grow for another 5 d before stress treatment was given.

For salt stress, seedlings were transferred aseptically on to 8 layers of tissue paper soaked with 250 mM NaCl solution in half strength MS basal without sucrose. The Petri-plates were sealed to prevent evaporation. They were allowed to grow for 4 days under culture room condition as given above. Subsequently, they were washed briefly in sterile distilled water, excess water soaked on sterile tissue paper and placed back on half strength MS basal without sucrose. They were allowed to grow under culture room conditions for recovery. Percentage green seedlings and fresh weight of the WT (untransformed control) and the transgenic lines were measured after 8 days of salt stress.

For cold treatment, Petri-plates containing 21-d-old seedlings were transferred to a cold chamber maintained at 8±1° C. for 15 d. The plates were then transferred back to culture room conditions for recovery. The fresh weight of the WT (untransformed control) and the transgenic lines were measured after allowing them to recover for 15 days following cold stress. All experiments were repeated more than twice and data of two experiments with variation are given.

For drought stress, the seeds were germinated on 0.3 M and 0.4 M mannitol and observations recorded over a period of 8 days. Relative fresh weight increase of the WT (untransformed control) and the transgenic lines were measured following 8 days of germination on 0.3 M and 0.4 M mannitol.

REFERENCES

1) Abe, H., Yamaguchi-Shinozaki, K., Urao, T., Iwasaki, T., Hosokawa, D., & Shinozaki, K. (1997) *Plant Cell* 9, 1859-1868.
2) Aharoni, A., & Vorst, O. (2001) *Plant Mol. Biol.* 48, 99-118.
3) Ausubel, F. M. (2002) *Plant Physiol.* 129, 394-437.
4) Beyaert, R., Heyninck, K., & van Huffel, S. (2000) *Biochem. Pharmacol.* 15, 1143-1151.
5) Brent, R. (2000) *Cell* 100, 169-183.
6) Burr, B. (2002) *Plant Cell* 14, 521-523.
7) Cantrell, R. P., & Reeves, T. G. (2002) *Science* 296, 53.
8) Cooper, J. T., Stroka, D. M., Brostjan, C., Palmetshofer, A., Bach, F. H., & Ferran, C. (1996) *J. Biol. Chem.* 271, 18068-18073.
9) De Valck, D., Heyninck, K., Van Criekinge, W., Vandenabeele, P., Fiers, W., & Beyaert, R. (1997) *Biophys. Biochem. Res. Commun.* 238, 590-594.
10) De Valck, D., Heyninck, K., Van Criekings, W., Contreeras, R., Bayaert, R., & Fiers, W. (1996) *FEBS Lett.* 384, 61-64.
11) Duan, W., Bingang, S., Li, T. W., Tan, B. J., Lee, M. K., & Teo, T. S. (2000) *Gene* 256, 113-121.
12) Evans, P. C., Taylor, E. R., Coadwell, J., Heyninck, K., Beyaert, R., & Kilshaw, P. J. (2001) *Biochem. J.* 357, 617-623.
13) Gelvin, S. B., & Schilperoort, R. A. (1994) *Plant Molecular Biology Manual* (Kluwer Academic Publishers, Dordrecht.)
14) Goff, S. A., Ricke, D., Lan, T-H., Presting, G., Wang, R., Dunn, M., Glazebrook, J., Sessions, A., Oeller, P., Varma, H., et al. (2002) *Science* 296, 92-100.
15) Grover, M., Dhingra, A., Sharma, A. K., Maheshwari S. C., & Tyagi, A. K. (1999) *Physiol. Plant.* 105, 701-707.
16) Hasegawa, M., Bressan, R., Zhu, J-K., & Bohnert H. J. (2000) *Annu. Rev. Plant Physiol. Plant Mol. Biol.* 51, 463-499.
17) Heyninck, K., De Valck, D., Vanden Berghe, W., Van Criekinge, W., Contreras, R., Fiers, W., Haegernan, G., & Beyaert, R. (1999a) *J. Cell Biol.* 145: 1471-1482.
18) Heyninck, K., Denecker, G., De Valck, D., Fiers, W., & Beyaert, R. (1999b) *Anticancer Res.* 19, 2863-2868.
19) Hughes, M. A., & Dunn, M. A. (1996) *J. Exp. Bot.* 47, 291-305.
20) Ingram, I., & Bartels, D. (1996) *Annu. Rev. Plant Physiol. Plant Mol. Biol.* 47, 377403.
21) Jani, D., Meena, L. S., Haq, Q. M. R., Singh, Y., Sharma, A. K., and Tyagi, A. K. (2002) *Transgenic Res.* 11, 447454.
22) Kamalay, J. C., & Goldberg, R. B. (1980) *Cell* 19, 935-946.
23) Kamalay, J. C., & Goldberg, R. B. (1984) *Proc. Nad. Acad. Sci. USA* 81, 2801-2805.
24) Kawasaki, S., Borchert, C., Deyholos, M., Wang, H., Brazille, S., Kawai, K., Galbraith, D., & Bohnert, H. J. (2001) *Plant Cell* 13, 889-905.
25) Khush, G. S. (1997) *Plant Mol. Biol.* 35, 25-34.
26) Khush, G. S. (1999) *Genome* 42, 646-655.
27) Kim, C. K., Lee, S. H., Cheong, Y. H., Yoa, C. M., Lee, I. S., Chun, H. J., Yun, D. J., Hong, J. C., Lee, J. C., Lim, C. O., & Cho, M. J. (2001) *Plant J.* 25, 247-259.
28) Kiyosue, T., Yamaguchi-Shinozaki, K., & Shinozaki, K. (1994) *Plant Cell Physiol.* 35, 225-231.
29) Lademann, U., Kallunki, T., & Jaattela, M. (2001) *Cell Death Differ.* 8, 265-272.
30) Lescot, M., Dehais, P., Thijis, G., Marchal, K., Moreau, Y., Van de Peer, Y., Rouze, P., & Rombauts, S. (2002) *Nucl. Acid Res.* 30, 325-327.
31) Linnen, J. M., Bailey, C. P., & Weeks, D. L. (1993) *Gene* 128, 181-188.
32) Logemann, J., Schell., J., & Willmitzer, L. (1987) *Anal. Biochem.* 163, 16-20.
33) Mohanty, A., Sarma, N. P., & Tyagi, A. K. (1999) *Plant Sci.* 147, 127-137.
34) Moons, A., Keyser, A. D., & Van Montagu, M. (1997) *Gene* 191, 197-204.
35) Opipari A. W. Jr., Boguski, M. S., & Dixit V. M. (1990) *J. Biol. Chem.* 265, 14705-14708.
36) Örvar, B. L., Sangwan, V., Omann, F., & Dhindsa, R. S. (2000) *Plant J.* 23, 785-794.
37) Piao, H. L., Lim, J. H., Kim, S. J., Cheong, G.-W., & Hwang, I. (2001) *Plant J.* 27, 305-314.
38) Prändl, R., Hinderhofer, K., Eggers-Schumacher, G., & Schöffl, F. (1998) *Mol. Gen. Genet.* 258, 269-278.
39) Ronald, P., & Leung, H. (2002) *Science* 296, 58-59.
40) Ruben, S. M., Dillon, P. J., Schreck R., Henkel. T., Chen, C. H., Maher, M., Baeuerle, P. A., & Rosen, C. A. (1991) *Science* 251, 1490-1493.
41) Saijo, Y., Hata, S., Kyozuka, J., Shimamoto, K., & Izui, K. (2000) *Plant J.* 23, 319-327.
42) Sambrook, J., Fritsh, E. F., & Maniatis, T. (1989) *Molecular Cloning: A Laboratory Manual* (Cold Spring Harbor Laboratory Press, New York).
43) Sangwan, V., Foulds, I., Singh, J., & Dhindsa, R. S. (2001) *Plant J.* 27, 1-12.
44) Satou, Y., & Satoh, N. (1997) *Dev. Biol.* 192, 467-481.
45) Scott, D. A., Greinwald, Jr. J. H., Marietta, J. R., Drury, S., Swidersid, R. E., Vinas, A., DeAngelis, M. M., Cari, R., Ramesh, A., Kraft, M. L., et al. (1998) *Gene* 215, 461-469.
46) Seki, M., Narusaka, M., Abe, H., Kasuga, M., Yamaguchi-Shinozaki, K., Carninci, P., Hayashizaki, Y., & Shinozald, K. (2001) *Plant Cell* 13, 61-72
47) Sharma, Y. K., Hinojos, C. M., & Mehdy, M. C. (1992) *Mol. Plant Microbe Interact.* 5, 89-95.
48) Shinozaki, K., & Yamaguchi-Shinozaki, K. (1997) *Plant Physiol.* 115, 327-334.
49) Song, H. Y., Rothe, M., & Goeddel, D. V. (1996) *Proc. Natl. Acad. Sci. USA* 93, 6721-6725.
50) Sun, W., Bernard, C., van de Cotte, B., Van Montagu, M., & Verbruggen, N. (2001) *Plant J.* 27, 407-415.
51) Taminen, I., Makela, P., Heino, P., & Palva, E. T. (2001) *Plant J.* 25, 1-8.
52) The *Arabidopsis* Genome Initiative (2000) *Nature* 408, 796-815.
53) Thomashow, M. F. (1998) *Plant Physiol.* 118, 1-7.
54) Thomashow, M. F. (1999) *Annu. Rev. Plant Physiol. Plant. Mol. Biol.* 50, 571-599.
55) Tokuhisa, J., & Browse, J. (1999) *Genet. Engg.* 21, 79-93.
56) Tyagi, A. K., & Mohanty, A. (2000) *Plant Sci.* 158, 1-18.
57) Tyagi, A. K., Mohanty, A., Bajaj, S., Chaudhury, A., & Maheswari, S. C. (1999) *Crit. Rev. Biotechnol.* 19, 41-79.
58) Urao, T., Katagiri, T., Mizoguchi, T., Yamaguchi-Shinozaki, K, Hayashida, N., & Shinozaki, K. (1994) *Mol. Gen. Genet.* 244, 331-340.
59) Welin, B. V., Olson, A., Nylander, M., & Tapio Palva, E. (1994) *Plant Mol. Biol.* 26, 131-144.
60) Xu, D., Duan, X., Wang, B., Hong, B., Ho, T. H. D., & Wu, R. (1996) *Plant Physiol.* 110, 249-257.

61) Yamaguchi-Shinozaki, K., & Shinozaki, K. (1993) *Plant Physiol.* 101, 1119-1120.
62) Yamaguchi-Shinozaki, K, & Shinozaki, K. (1994) *Plant Cell* 6, 251-264.
63) Yu, J., Hu, S., Wang, J., Wong, G. K., Li, S., Liu, B., Deng, Y.; Dai L., Zhou, Y., Zhang, X., et al. (2002) *Science* 296, 79-92.
64) Zhu, J. K. (2002) *Annu. Rev. Plant Biol.* 53, 247-273

---

We claim:

1. A method of increasing abiotic stress tolerance in a plant, said method comprising transforming said plant with a recombinant vector comprising a polynucleotide sequence set forth in SEQ ID NO: 1 or a variant thereof coding for a polypeptide sequence as shown in SEQ ID NO: 2, and expressing the polynucleotide sequence or the variant thereof to yield a transformed plant.

2. The method of claim 1, wherein said plant used for transformation is selected from a group consisting of tobacco, rice and tomato plant.

3. The method of claim 1, wherein said method provides said transformed plant having increased tolerance to cold stress relative to an untransformed plant of the same plant species.

4. The method of claim 1, wherein said method provides said transformed plant having increased tolerance to drought stress relative to an untransformed plant of the same plant species.

5. The method of claim 1, wherein said method provides said transformed plant having increased tolerance to salt stress relative to an untransformed plant of the same plant species.

6. A transgenic plant, plant tissue or plant cell produced by the method of claim 1, wherein said transformed plant, plant tissue or plant cell exhibits increased tolerance to cold stress relative to an untransformed plant of the same plant species.

7. A transgenic plant, plant tissue or plant cell produced by the method of claim 1, wherein said transformed plant, plant tissue or plant cell exhibits increased tolerance to drought stress relative to an untransformed plant of the same plant species.

8. A transgenic plant, plant tissue or plant cell produced by the method of claim 1, wherein said transformed plant, plant tissue or plant cell exhibits increased tolerance to salt stress relative to an untransformed plant of the same plant species.

9. Transgenic seeds produced by the transgenic plant of claim 6, wherein the seeds comprise the polynucleotide sequence.

10. Transgenic seeds produced by the transgenic plant of claim 7, wherein the seeds comprise the polynucleotide sequence.

11. Transgenic seeds produced by the transgenic plant of claim 8, wherein the seeds comprise the polynucleotide sequence.

* * * * *

UNITED STATES PATENT AND TRADEMARK OFFICE
CERTIFICATE OF CORRECTION

| | | |
|---|---|---|
| PATENT NO. | : 7,576,263 B2 | Page 1 of 1 |
| APPLICATION NO. | : 10/540956 | |
| DATED | : August 18, 2009 | |
| INVENTOR(S) | : Tyagi et al. | |

It is certified that error appears in the above-identified patent and that said Letters Patent is hereby corrected as shown below:

(2)    Face of the Patent, See Item (56) References Cited, OTHER PUBLICATIONS, Column 2, the second to last entry to Mohanty et al., "high prequency" should read --high frequency--

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,576,263 B2  Page 1 of 1
APPLICATION NO. : 10/540956
DATED : August 18, 2009
INVENTOR(S) : Tyagi et al.

It is certified that error appears in the above-identified patent and that said Letters Patent is hereby corrected as shown below:

Title Page;

(1)  <u>Face of the Patent</u>. See Item (73) Assignee: the second assignee is missing.
Item (73) should read:
-- University of Delhi, New Delhi (IN) and
   Department of Biotechnology, New Delhi (IN) --

Signed and Sealed this

Second Day of November, 2010

David J. Kappos
*Director of the United States Patent and Trademark Office*